United States Patent
Zimmerman et al.

(10) Patent No.: US 10,799,192 B2
(45) Date of Patent: Oct. 13, 2020

(54) METHOD AND APPARATUS FOR PARTIAL VOLUME IDENTIFICATION FROM PHOTON-COUNTING MACRO-PIXEL MEASUREMENTS

(71) Applicant: Canon Medical Systems Corporation, Otawara-shi (JP)

(72) Inventors: Kevin Christopher Zimmerman, Sturtevant, WI (US); Liang Cai, Vernon Hills, IL (US); Hiroaki Miyazaki, Otawara (JP); Xiaohui Zhan, Vernon Hills, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 171 days.

(21) Appl. No.: 16/182,156

(22) Filed: Nov. 6, 2018

(65) Prior Publication Data
US 2020/0138386 A1    May 7, 2020

(51) Int. Cl.
*A61B 6/03* (2006.01)
*G06T 11/00* (2006.01)
*G06T 7/62* (2017.01)

(52) U.S. Cl.
CPC .............. *A61B 6/032* (2013.01); *G06T 7/62* (2017.01); *G06T 11/008* (2013.01)

(58) Field of Classification Search
CPC .......... A61B 6/032; G06T 11/008; G06T 7/62
See application file for complete search history.

(56) References Cited

U.S. PATENT DOCUMENTS 8,422,826 B2   4/2013   Holt
9,687,207 B2   6/2017   Zou et al.
(Continued)

OTHER PUBLICATIONS

Jiang Hsieh, "Computed Tomography: Principles, Design, Artifacts, and Recent Advances", SPIE Press Monograph, The International Society for Optical Engineering, vol. PM188, $2^{nd}$ Revised Edition, Nov. 19, 2009, 560 pages (Abstract only).

(Continued)

*Primary Examiner* — Wayne H Cai
(74) *Attorney, Agent, or Firm* — Oblon, McClelland, Maier & Neustadt, L.L.P.

(57) ABSTRACT

A method and apparatuses are provided to identify and correct partial volume errors (PVEs) in material decomposition of a spectral computed tomography (CT) scan, due to different X-ray trajectories incident on a same macro-pixel passing through different material components (e.g., bone and water). Macro-pixels are virtual crystals generated by aggregating the signals/counts from several smaller actual pixels (i.e., micro-pixels) of a detector array. Thus, when a PVE is identified within a macro-pixel, the separate signals/counts from the micro-pixels can be used for material decomposition, instead of the aggregated signals/counts of the macro-pixel, thereby providing improved spatial resolution of the material components and, at least partial, overcoming the PVE. A measure of the difference between spectrally-resolved counts based a material projection lengths (e.g., from a calibrated lookup table) and the measured counts of the macro-pixel can be used to identify PVEs, e.g., when the difference measure exceeds a predefined threshold.

23 Claims, 9 Drawing Sheets

(56) References Cited

U.S. PATENT DOCUMENTS

2015/0348292 A1* 12/2015 Taguchi .................. A61B 6/032
                                                          382/131
2017/0023496 A1    1/2017 Persson
2018/0293762 A1* 10/2018 Fu ......................... G06T 11/003

OTHER PUBLICATIONS

Thorsten M. Buzug, "Computed tomography: From Photon Statistics to Modern Cone-Beam CT", Springer Science & Business Media, 1$^{st}$ Edition, 2008, 522 pages (Abstract only).

Mats Persson, et al., "Resolution improvement in x-ray imaging with an energy-resolving detector", Proceedings of SPIE Physics of Medical Imaging, vol. 10132, Mar. 9, 2017, 9 pages.

G. H. Glover, et al., "Nonlinear partial volume artifacts in x-ray computed tomography", Medical Physics, vol. 7, No. 3, May/Jun. 1980, pp. 238-248.

\* cited by examiner

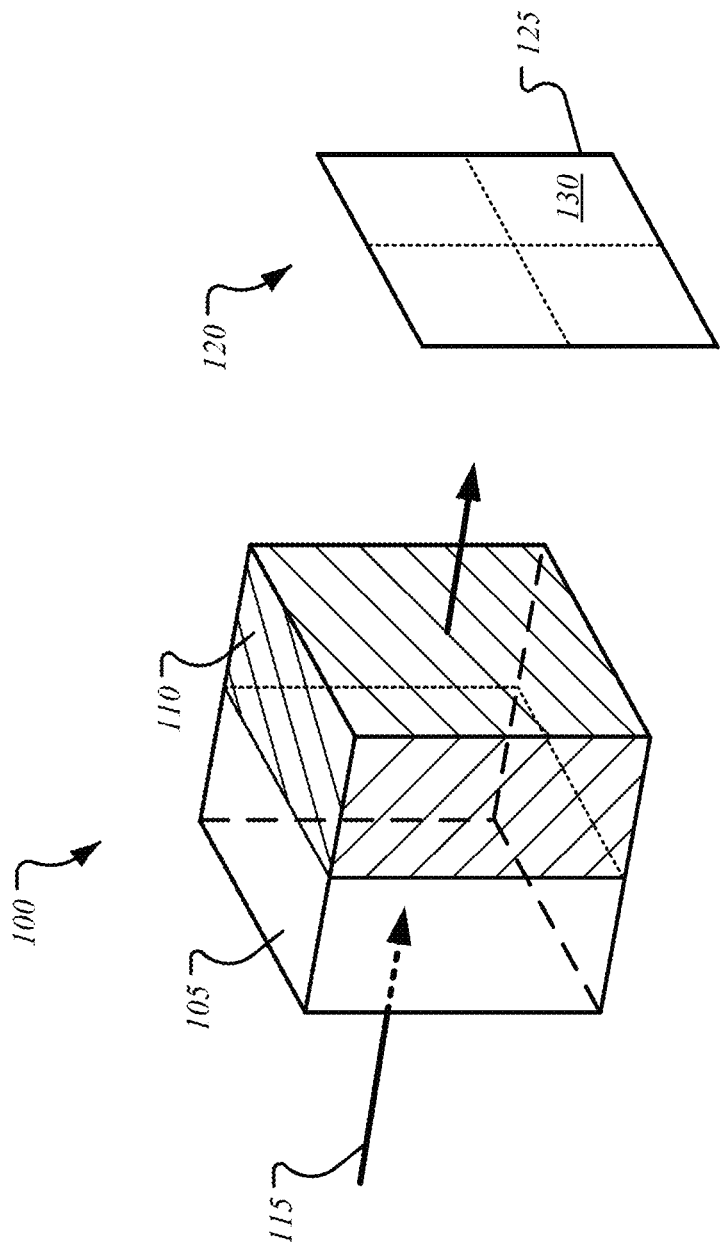

METHOD AND APPARATUS FOR PARTIAL VOLUME IDENTIFICATION FROM PHOTON-COUNTING MACRO-PIXEL MEASUREMENTS

BACKGROUND

Field

Embodiments described herein relate generally to material decomposition of photon-counting spectral computed tomography data, and, more particular, to identifying partial volume errors (PVEs) when the material decomposition fails to converge and then correcting the PVE by using projection data from micro-pixels, rather than macro-pixels, for the material decomposition, wherein a macro-pixel is virtual pixel that aggregates the signals of multiple pixels within a detector array e.g., the micro-pixels).

Description of the Related Art

Computed tomography (CT) systems and methods are widely used, particularly for medical imaging and diagnosis. CT systems generally create projection images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body in the projection plane. The attenuation of the radiation that has passed through the body is measured by processing electrical signals received from the detector. In some implementations a multi slice detector configuration is used, providing a volumetric projection of the body rather than planar projections.

Typically the X-ray source is mounted on a gantry that revolves about a long axis of the body. The detectors are likewise mounted on the gantry, opposite the X-ray source. A cross-sectional image of the body is obtained by taking projective attenuation measurements at a series of gantry rotation angles, transmitting the projection data/sinogram to a processor via the slip ring that is arranged between a gantry rotor and stator, and then processing the projection data using a CT reconstruction algorithm (e.g., inverse Radon transform, a filtered back-projection, Feldkamp-based cone-beam reconstruction, iterative reconstruction, or other method). For example, the reconstructed image can be a digital CT image that is a square matrix of elements (pixels), each of which represents a volume element (a volume pixel or voxel) of the patient's body. In some CT systems, the combination of translation of the body and the rotation of the gantry relative to the body is such that the X-ray source traverses a spiral or helical trajectory with respect to the body. The multiple views are then used to reconstruct a CT image showing the internal structure of the slice or of multiple such slices.

Conventionally, energy-integrating detectors have been used to measure CT projection data. Now, photon-counting detectors (PCDs) present a feasible alternative to energy-integrating detectors. PCDs have many advantages including their capacity for performing spectral CT and the ability to divide the scan area into many smaller "pixels" of detectors for greater resolution. While semiconductor-based PCDs provide unique advantages for spectral CT, they also create unique challenges. For example, due to pulse pile up, PCDs can exhibit a nonlinear response with respect to X-ray flux. Without correcting for nonlinearities and spectral shifts in the detector response, images reconstructed from semiconductor-based PCDs can have poorer image quality.

One advantage of PCDs is that they can be used for spectral CT because they provide information regarding the change in X-ray attenuation as a function of the energies of the X-rays. Spectral CT is desirable because different materials, such as bone and water, exhibit different spectral absorption signatures, enabling a spectral resolved CT scan to be decomposed into material components. This material decomposition can however result in partial volume errors (PVEs) when the pixels of the X-ray detector are large enough that X-rays falling within a same pixel of the X-ray detector pass through dissimilar materials. Accordingly, better methods of identifying and correcting PVEs are desired.

BRIEF DESCRIPTION OF THE DRAWINGS

A more complete understanding of this disclosure is provided by reference to the following detailed description when considered in connection with the accompanying drawings, wherein:

FIG. 2A illustrates a schematic of a perspective view of partial volume averaging for a voxel having two materials arranged in an orthogonal configuration relative to a beam direction, according to an exemplary embodiment of the disclosure;

DETAILED DESCRIPTION

Figure 1:
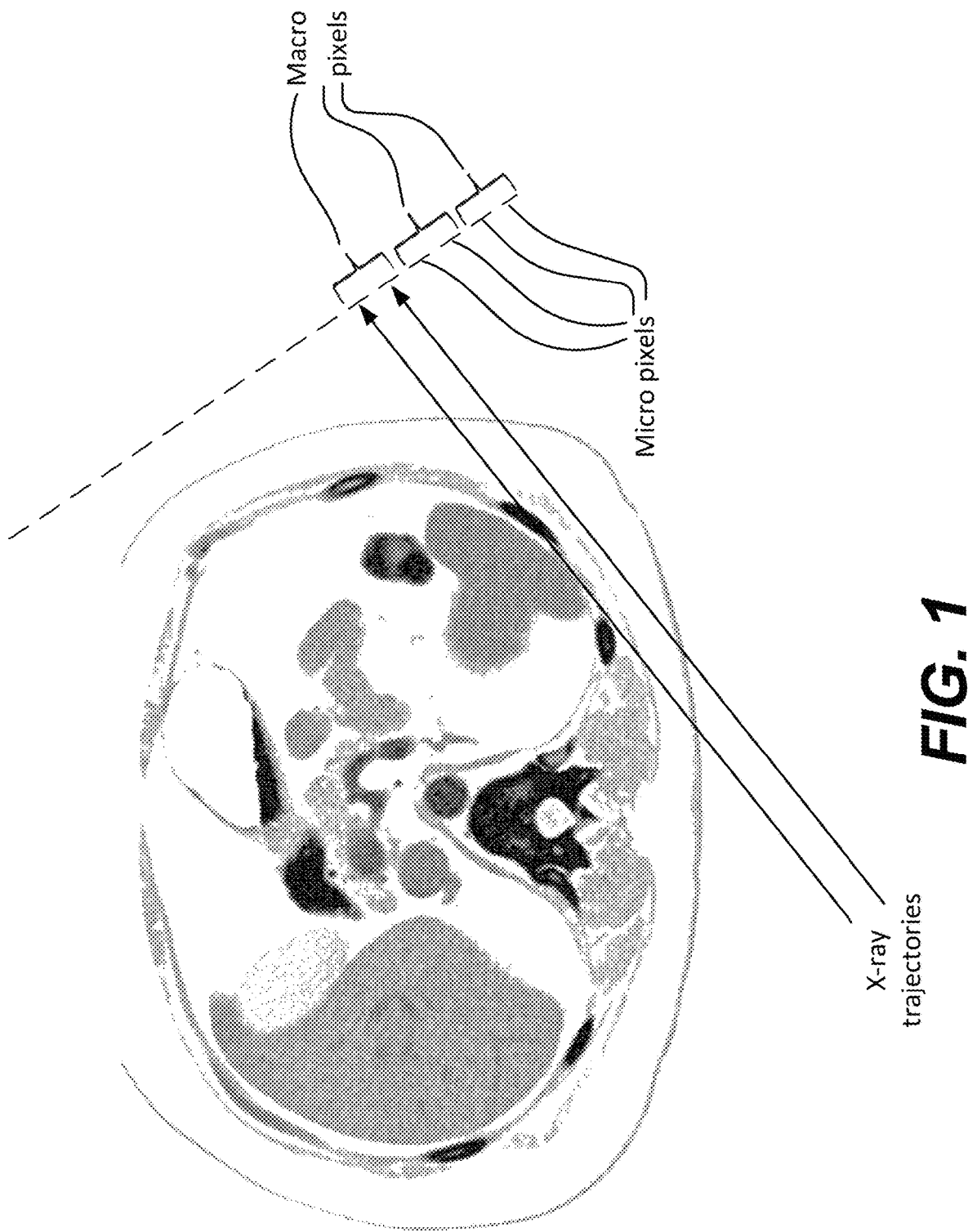
FIG. 1 illustrates a partial volume effect when macro pixel aggregates the signals/counts of a micro pixel detecting X-rays passing through only soft-tissues together with a micro pixel detecting X-rays that pass through bone in addition to passing through soft-tissues, according to an exemplary embodiment of the disclosure.

The description set forth below in connection with the appended drawings is intended as a description of various aspects of the disclosed subject matter and is not necessarily intended to represent the only aspect(s). In certain instances, the description includes specific details for the purpose of providing an understanding of the disclosed subject matter. However, it will be apparent to those skilled in the art that aspects may be practiced without these specific details. In some instances, well-known structures and components may be shown in block diagram form in order to avoid obscuring the concepts of the disclosed subject matter.

Reference throughout the specification to "one aspect" or "an aspect" means that a particular feature, structure, characteristic, operation, or function described in connection with an aspect is included in at least one aspect of the disclosed subject matter. Thus, any appearance of the phrases "in one aspect" or "in an aspect" in the specification is not necessarily referring to the same aspect. Further, the particular features, structures, characteristics, operations, or functions may be combined in any suitable manner in one or more aspects. Further, it is intended that aspects of the disclosed subject matter can and do cover modifications and variations of the described aspects.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "top," "bottom," "front," "rear," "side," "interior," "exterior," and the like that may be used herein, merely describe points of reference and do not necessarily limit aspects of the disclosed subject matter to any particular orientation or configuration. Furthermore, terms such as "first," "second," "third," etc., merely identify one of a number of portions, components, points of reference, operations and/or functions as described herein, and likewise do not necessarily limit aspects of the disclosed subject matter to any particular configuration or orientation.

As discussed above, photon-counting detectors (PCDs) provide several advantages for CT, including the advantage that material decomposition can be performed using spectrally resolved projection data. However, several obstacles can limit the realization of the full potential of PCDs. As discussed above, at high X-ray flux rates, pulse pile up result in a nonlinear response for PCDs. To avoid pile up, the cross-sectional area of the PCDs can be decreased, pushing the onset of pulse pile up to higher X-ray fluxes. For example, a single large PCD can be sub-divided into four smaller PCDs, each covering ¼$^{th}$ the area of the large PCD with the flux rate per small PCD being ¼ that of the large PCD. In practice, charge sharing and other effects can fundamentally limit how small PCDs can be made.

For example, subdividing the PCDs into smaller PCDs can increase the total number of detector elements/pixels in a CT scanner, resulting in a communications bottleneck between the rotor and stator of a CT gantry based on how fast the projection data can be transmitted from the rotating annular structure on which the X-ray detectors are arranged across a slip ring to the fixed gantry structure that houses one or more computer processors performing image reconstruction, etc. That is, acquiring data at a higher resolution results in more data to be transmitted across the slip ring in a given amount of time, exceeding the limited communication bandwidth available via the slip ring. The slip ring is a non-limiting example of a rotor-to-stator communications device and, in certain implementations, a fiber optic rotary joint or other communication device can be used instead of a slip ring, as would be understood by a person of ordinary skill in the art.

To overcome this communication bottleneck, the counts from the small PCDs (e.g., micro-pixels) can be aggregated as a count of a virtual large PCD (e.g., a macro-pixel), reducing the amount of data to be transmitted.

Although this strategy helps to address the pileup issue, aggregating micro-pixel counts into macro-pixel counts leaves the projection data susceptible to partial volume errors (PVEs). The methods described herein address PVEs by identifying macro-pixels in which PVEs occur and then using the micro-pixel counts, rather than the macro-pixel counts, to correct the PVEs.

Referring now to the drawings, wherein like reference numerals designate identical or corresponding parts throughout the several views, FIG. 1 shows cross-section of a torso and two parallel X-ray trajectories passing through the torso on their way to respective micro-pixels in a detector array. The micro-pixels corresponding to the two X-ray trajectories are aggregated/averaged to generate a signal for a macro-pixel. For the two X-ray trajectories shown, one X-ray trajectory passes through only soft tissues, whereas the other X-ray trajectory passes through bone (e.g., a rib) in addition to passing through soft tissues. Consequently, when the two micro-pixels signals corresponding to these two X-ray trajectories are combined to generate a macro-pixel signal, material decomposition of the resulting macro-pixel signal will be imperfect due to the partial volume effect, ultimately resulting in a PVE. When the PVE is identified based on the failure of the material decomposition to converge, the material decomposition can then be corrected by performing material decomposition on the micro-pixels signals, rather than the macro-pixel signal, as described in more detail below. This failure of the material decomposition to converge can be indicated by a non-negligible difference between the measured counts $\tilde{N}$ of the macro-pixel and calibrated/theoretical counts $\vec{N}(\vec{L})$ based on material projection lengths $\vec{L}$.

Accordingly, PVEs can occur when different materials occupy different regions within the cross-sectional area of the X-ray trajectories falling within a recorded pixel (e.g., a macro-pixel) of a CT scan. The methods described herein provide the advantageous effects of identifying and correcting these PVEs, thereby resulting in more accurate material decomposition and reconstructed images.

Material decomposition of spectral CT data is possible because materials having atoms with different atomic number Z have different spectral profiles for attenuation. Apart from k-edge effects, the spectral shape of X-ray attenuation in biological materials is determined by two physical processes-photoelectric attenuation and Compton scattering. Thus, the attenuation coefficient as a function of energy can be approximated by the decomposition $$\mu(E,x,y)=\mu_{PE}(E,x,y)+\mu_{C}(E,x,y),$$

wherein $\mu_{PE}(E,x,y)$ is the photoelectric attenuation and $\mu_C(E,x,y)$ is the Compton attenuation. This attenuation coefficient can be rearranged instead into a decomposition of a material 1 (e.g., a high-Z material such as bone) and a material 2 (e.g., a low-Z material such as water) to become $$\mu(E,x,y)\approx\mu_1(E)c_1(x,y)+\mu_2(E)c_2(x,y),$$

where $c_{1,2}(x,y)$ is a spatial function describing the concentrations of material 1 and material 2 located at position (x,y).

When the voxels are approximately spatial uniform in material composition the intensity along a given X-ray trajectory can be given by $$I = I_0 e^{-(\mu_1 L_1 + \mu_2 L_2)},$$

wherein $L_1 = \int dl\, c_1(x,y)$ is the projection length of the first material component, $L_2 = \int dl\, c_2(x,y)$ is the projection length of the second material component, and the integrals are line integrals along the line $l(x,y)$ of the X-ray trajectory.

In spectral CT utilizing photon-counting detectors (PCDs), image reconstruction is preceded by pre-reconstruction steps including correcting for the detector response and material decomposition. Specifically, partial volume effects can result in anomalous spectral signatures due to averaging/aggregating adjacent pixel values corresponding to different material components.

Generally, the intensity I of a beam, for example an x-ray beam, transmitted through an absorbing material can be expressed as $$I = I_0 e^{-(\mu L)}$$

where $I_0$ is the initial beam intensity, L is the path length, and $\mu$ is the attenuation coefficient. The beam can be monochromatic or polychromatic in energy, wherein a polychromatic beam can include multiple X-ray energies, which can be used to extract energy-dependent attenuation coefficients. The spectrum term S(E) is the incident spectrum of energy E on the detector. This spectrum term for two materials is given by $$S(E) = S_0(E) \exp[-\mu_1(E) L_1 - \mu_2(E) L_2]$$

wherein $S_0$ is the energy spectrum from the source, $\mu_1$ and $\mu_2$ are the attenuation coefficients of the basis materials for the material decomposition, and $L_1$ and $L_2$ are the respective projection lengths. When PCDs are used to detect the X-rays, the energy spectrum can be divided into a series of n energy bins, with the number of counts $N_i$ in the $i^{th}$ energy bin, which is defined as the range $\{E_i, E_{i+1}\}$, of an $m^{th}$ detector element of a given pixel given by $$N_{i,m} \propto C \int_{E_i}^{E_{i+1}} dE \int_{x_m, y_m}^{x_{m+1}, y_{m+1}} dx\, dy\, S(E, x, y),$$

wherein C is a calibration constant, and the $m^{th}$ detector element has a detection area defined as $\{(x_m, y_m), (x_{m+1}, y_{m+1})\}$.

Figure 2B:
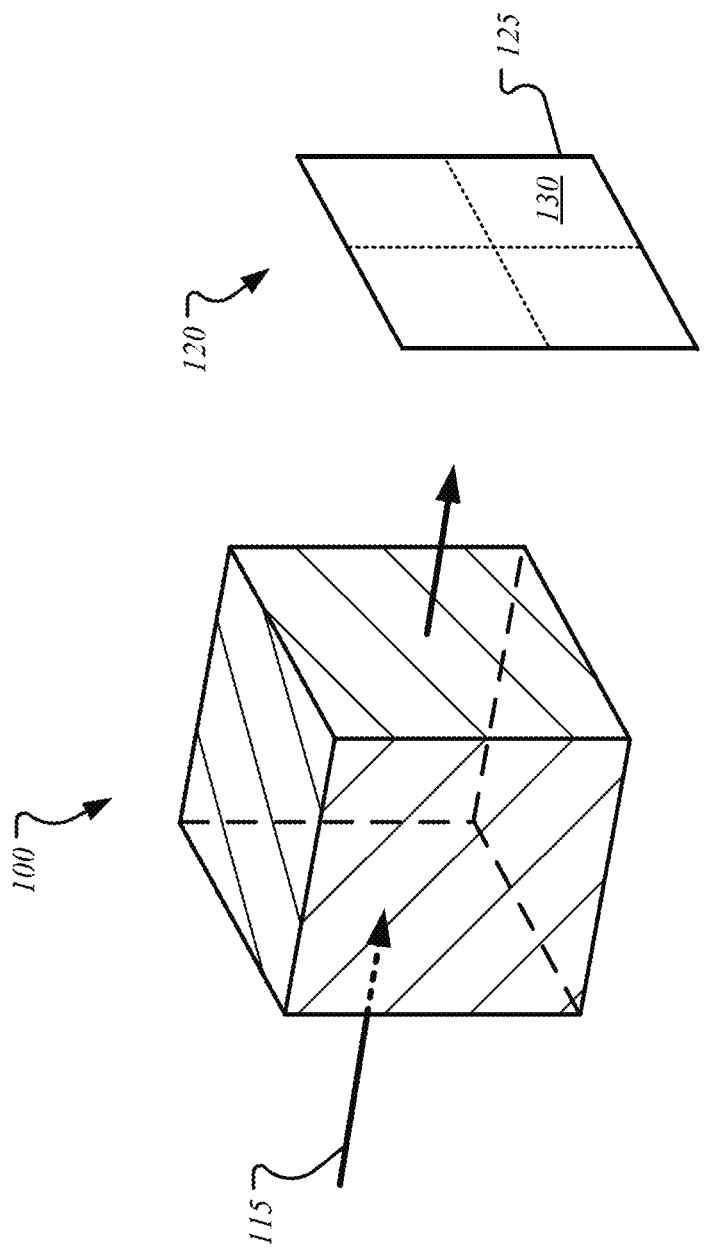
FIG. 2B illustrates a schematic of a perspective view of partial volume averaging for a voxel having a homogenous mixture of two materials, according to an exemplary embodiment of the disclosure.
Figure 2C:
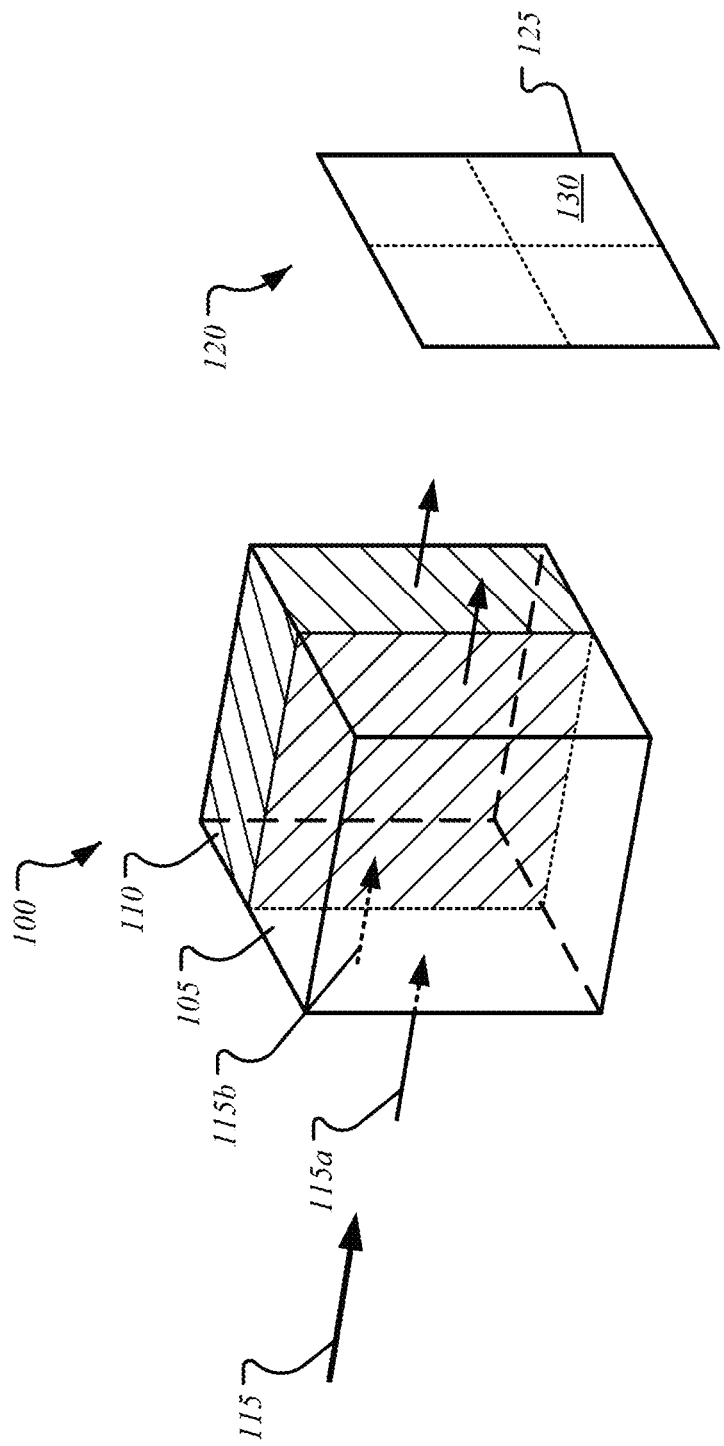
FIG. 2C illustrates a schematic of a perspective view of partial volume averaging for a voxel having two materials arranged in a parallel configuration relative to a beam direction, according to an exemplary embodiment of the disclosure.
Figure 3A:
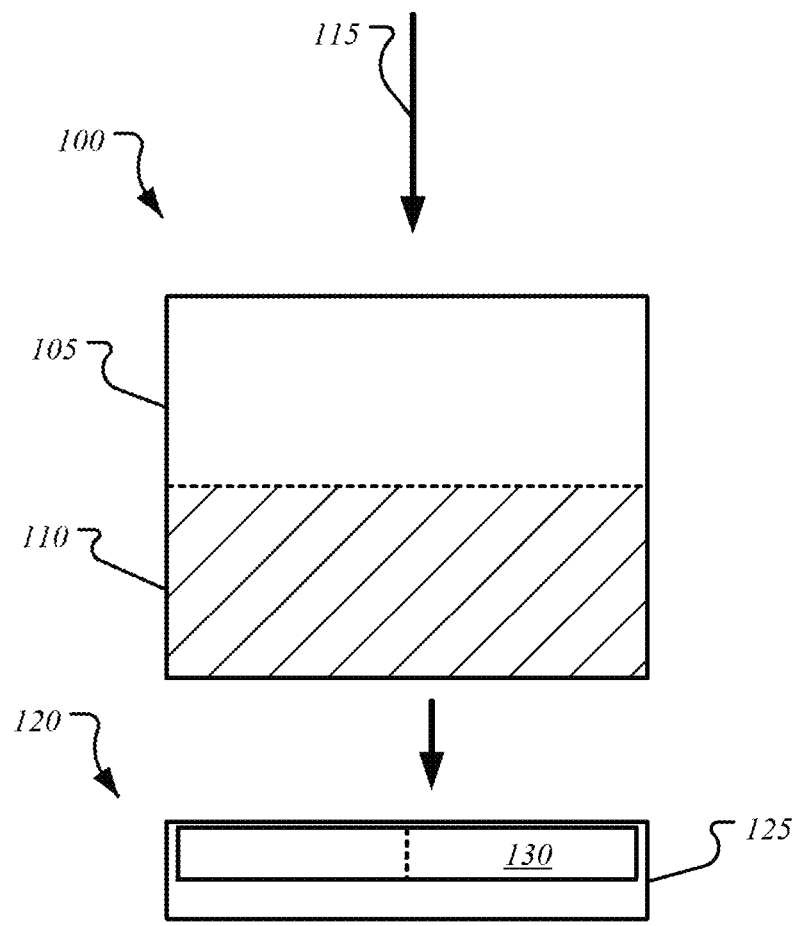
FIG. 3A illustrates a schematic of a side view of partial volume averaging for a voxel having two materials arranged in an orthogonal configuration relative to a beam direction, according to an exemplary embodiment of the disclosure.
Figure 3B:
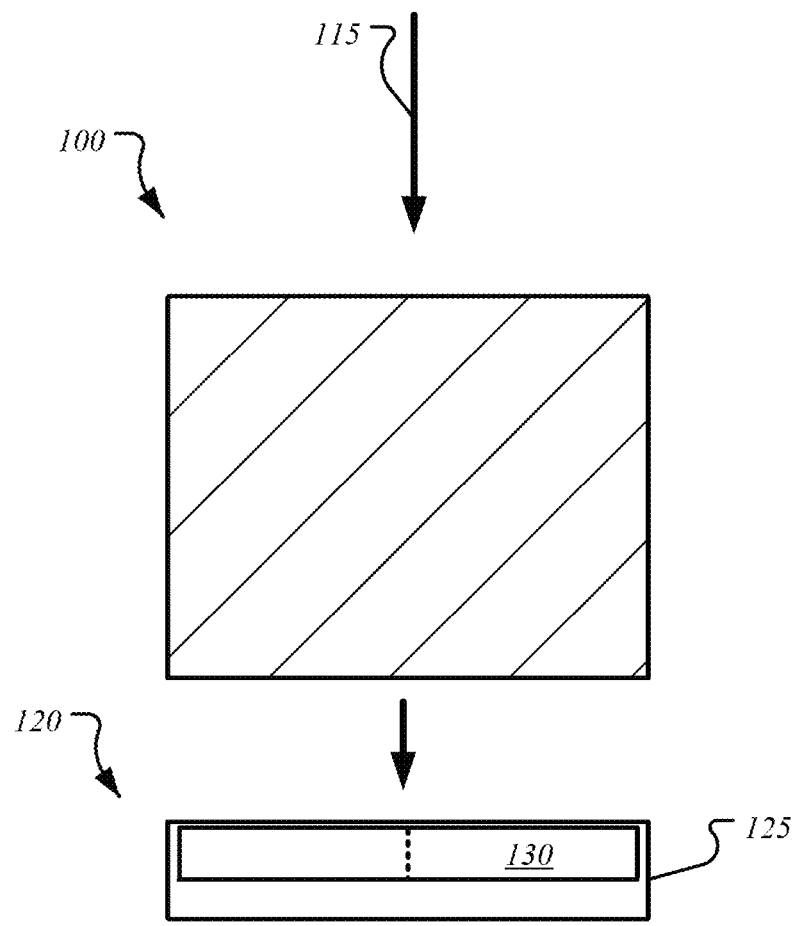
FIG. 3B illustrates a schematic of a side view of partial volume averaging for a voxel having a homogenous mixture of two materials, according to an exemplary embodiment of the disclosure.
Figure 3C:
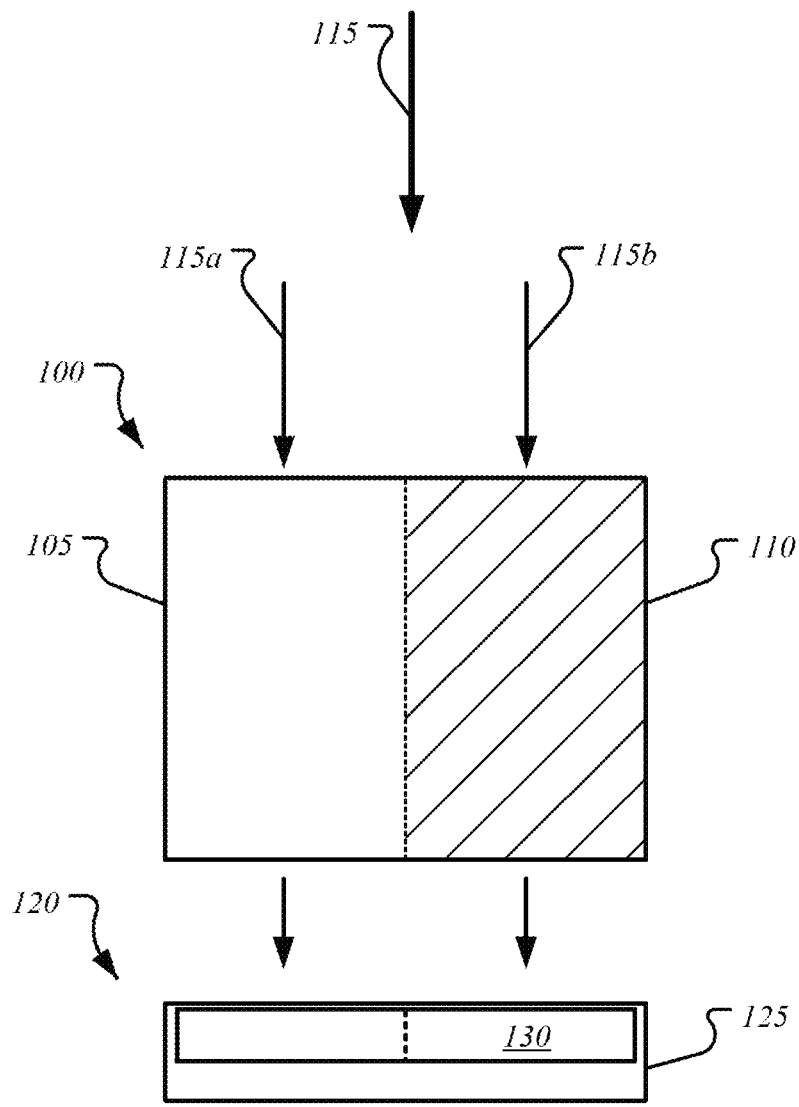
FIG. 3C illustrates a schematic of a side view of partial volume averaging for a voxel having two materials arranged in a parallel configuration relative to a beam direction, according to an exemplary embodiment of the disclosure.

FIGS. 2A, 2B, 3A, and 3B provide non-limiting simplified examples of scenarios in which PVEs do not occur FIG. 2A, whereas FIGS. 2C and 3C provide a non-limiting simplified example of a scenario in which PVEs does occur.

FIG. 2A illustrates a perspective view of partial volume averaging for a voxel 100 having two materials arranged in an orthogonal/series configuration, according to an exemplary aspect of the present disclosure. The orientation of a first material 105 and a second material 110 in the voxel 100 can be simplified as a sandwich structure, wherein the interface between the first 105 and second 110 materials is substantially orthogonal to a direction of a beam 115 of photons impinging on a detector 120. The beam 115 can be represented as a single ray traversing the voxel 100, or as multiple small rays averaged together to comprise the single ray. The detector 120 can be configured to receive a plurality of photons from the beam 115 and convert the energy of the impinged photon into an electrical signal. The detector 120 can be a photon-counting detector (PCD), wherein the electrical signal produced is converted to a photon count and analyzed by processing circuitry. In the orthogonal orientation, the beam 115, which has intensity $I_0$ upon entering the voxel 100, passes through the first material 105 having an attenuation $\mu_1$, and then the second material 110 having attenuation $\mu_2$, having an intensity I upon exiting the voxel 100. If the beam 115 passes through both materials having the same thickness as shown, the path length is half the length of the voxel 100 in each material. Thus, $L/2 = L_1 = L_2$, and the exiting intensity I of a monochromatic beam 115 can be expressed as $$I = I_0 \exp\left(-\frac{L}{2}(\mu_1 + \mu_2)\right).$$

A similar expression based on the aforementioned can be given in terms of the number of transmitted photons N, where $N_0$ is the incident number of photons, yielding $$N(E) = N_0(E) \exp\left(-\frac{L}{2}(\mu_1(E) + \mu_2(E))\right).$$

FIG. 2B illustrates a perspective view of partial volume averaging for a voxel 100 having a homogenous mixture of two materials, according to an exemplary aspect of the present disclosure. Here, the mixture of the first material 105 and the second material 110 results in the same transmission as FIG. 2A because the beam 115 effectively moves through a path length L/2 coinciding with the thickness for each material. Thus, the order of the materials through which the beam passes does not matter due to the exponential form of the attenuation as long as an effective path length of L/2 is traversed for both materials through a voxel 100 having length L. The number of transmitted photons N can then be expressed again as described above.

FIG. 2C illustrates a perspective view of partial volume averaging for a voxel 100 having two materials arranged in a parallel configuration, according to an exemplary aspect of the present disclosure. As the beam 115 rotates around an object while scanning, for example an additional 90° rotation, the beam 115 can move to a position where the interfacial plane between the first material 105 and the second material 110 is oriented substantially parallel to the beam 115. The beam 115 passing through the voxel 100 can include narrower rays that pass through the first material 105 and not through the second material 110, and vice versa. For the beam 115 represented as being comprised of the average of many rays in FIG. 2A and FIG. 2B, the beam 115 in FIG. 2C can be split into a first ray 115a passing through the first material 105 and a second ray 115b passing through the second material 110, wherein the first ray 115a will yield different results for the number of transmitted photons as compared to the second ray 115b when measured by the detector 120. The detector 120 can include a grid of at least one macro-pixels 125, wherein each of the at least one macro-pixels 125 can be divided into a plurality of micro-pixels 130. The micro-pixels 130 can be configured to detect the narrower first and second rays 115a, 115b and convert the imparted energy from the photons through each respective ray passing through each respective material into an electrical signal at each respective micro-pixel 130 to register separate photon counts. Since the first material 105 and the second material 110 have different attenuation coefficients, the transmitted number of photons (for a polychromatic beam 115) will be given by $$N(E) = \frac{N_0(E)}{2}(\exp(-L\mu_1(E)) + \exp(-L\mu_2(E)))$$

This differs from the previous expression from FIGS. 2A and 2B. Consequently, an attempt to decompose the spectral counts into material components will result in partial volume error (PVE) in this case. This PVE will be mitigated, however, if the measurement volume is sub-divided into smaller volumes corresponding to the micro-pixels 130, and the counts for micro-pixels 130 are utilized for the material decomposition instead of the counts for macro-pixel 125.

FIG. 3A illustrates a cross sectional view of the partial volume averaging for a voxel 100 having two materials arranged in an orthogonal configuration, according to an exemplary aspect of the present disclosure. As described in FIG. 2A, the first material 105 can form an interface with the second material 110 when adopting a stacked formation. In a simplified representation, this interface can be planar and substantially perpendicular relative to the direction of the beam 115. In this configuration, partial volume effects cannot introduce errors into the reading for N since the beam 115 passes through both materials 105, 110.

FIG. 3B illustrates a cross sectional view of the partial volume averaging for a voxel 100 having two materials homogenously mixed together, according to an exemplary aspect of the present disclosure. As described in FIG. 2B, the first material 105 and the second material 110 can be a homogenous mixture such that interfaces between the first and second materials 105, 110 are absent. However, since the mixture is homogenous, the beam 115 still passes through the voxel 100 with the same attenuation as it does in FIGS. 2A and 2A, and partial volume effects are not introduced.

FIG. 3C illustrates a cross sectional view of the partial volume averaging for a voxel 100 having two materials arranged in a parallel configuration, according to an exemplary aspect of the present disclosure. As described in FIG. 2C, the first material 105 can form an interface with the second material 110, wherein the interface can be planar and substantially parallel to the direction of the beam 115. If the beam 115 is comprised of many smaller rays 115a, 115b aggregated and averaged to produce the effective transmitted beam passing through the voxel 100, then this orientation of the first material 105 and the second material 110 can yield measurement errors due to partial volume effects. Thus, to reduce the measurement errors, the individual measurements of the plurality of micro-pixels 130 can be used for image reconstruction instead of the value of the at least one macro-pixels 125 (which are determined via averaging the values of the plurality of micro-pixels 130 per their respective macro-pixel 125).

Figure 4:
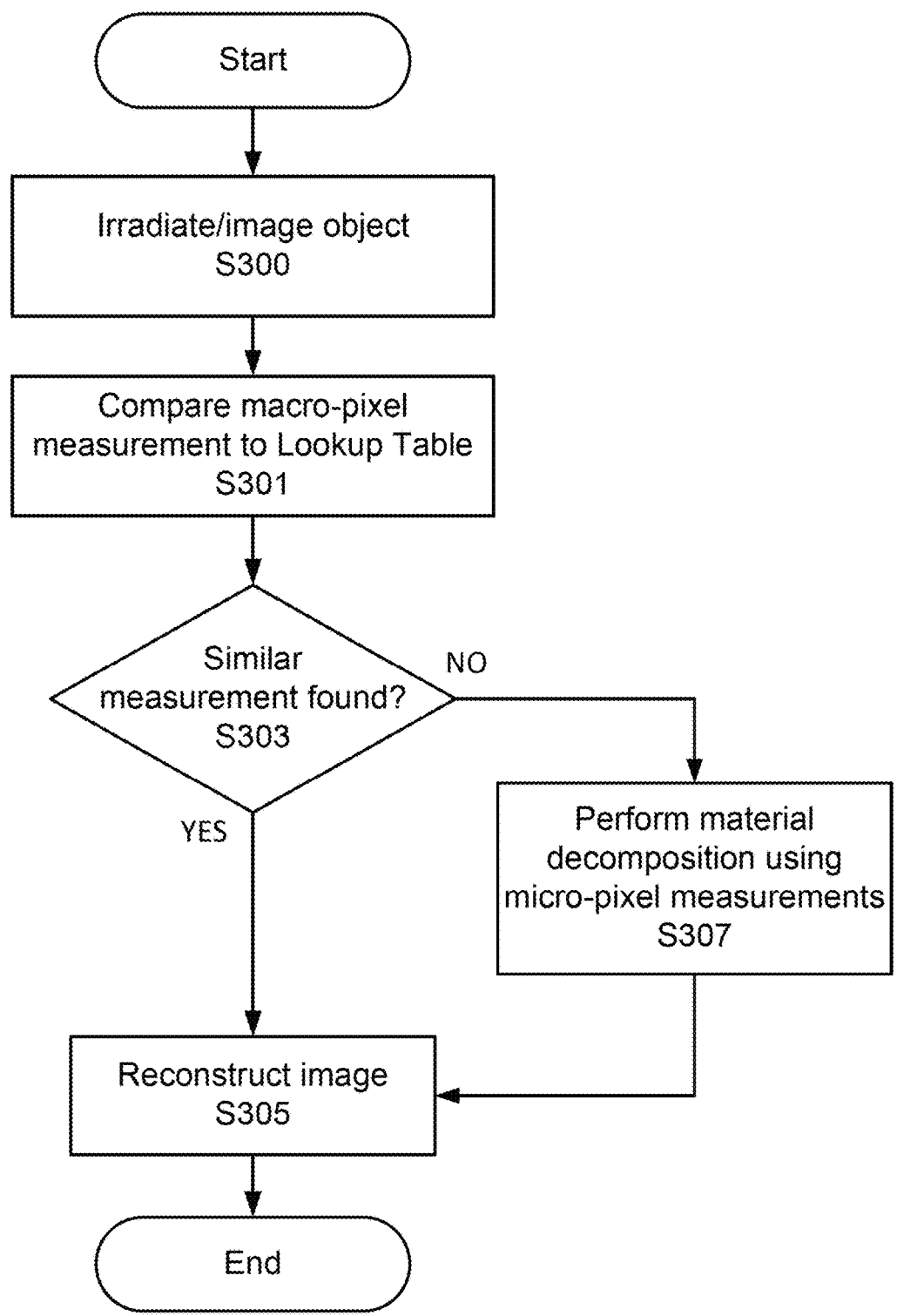
FIG. 4 illustrates a flow chart for a method of identifying partial volumes in a scan, according to an exemplary embodiment of the disclosure.

FIG. 4 shows a flow diagram of a non-limiting example of a method for identifying and correcting PVEs by switching to micro-pixel measurements from macro-pixel measurements.

In step S300, image acquisition is initiated.

In step S301, the detector 120 detects, for the $m^{th}$ micro-pixel of the micro-pixels 130 and for the $i^{th}$ energy bin, a number of counts $N_{i,m}^{(micro)}$. These counts are then aggregated to generate the counts for the $N_i$ of $i^{th}$ energy bin of the macro-pixel 125, which is given by $$N_i^{(macro)} = \sum_{m=1}^{4} N_{i,m}^{(micro)}.$$

In step S301, the measured counts $\tilde{N}=\{N_1^{(macro)}, N_2^{(macro)}, \ldots, N_n^{(macro)}\}$ are compared to counts $\vec{N}(\vec{L})$ for a material decomposition, wherein the material-decomposition counts $\vec{N}$ are a function of a vector of the projection lengths $\vec{L}$. For example, this comparison can be performed using an objective function φ (also referred to as a cost function or error measure), representing agreement between the measured counts $\tilde{N}$ and the material-decomposition counts $\vec{N}$. Several different definitions of the cost function φ($L_1,L_2$) can be used to represent a difference between the measured counts $\tilde{N}_i$ and the modeled counts $N_m$.

In one implementation, the cost function is the least squares of the difference between the measured counts $N'_m$ and the material-decomposition counts $\vec{N}$, i.e., $$\varphi = \sum_i (\tilde{N}_i - \vec{N}_i)^2.$$

In one implementation, the cost function is the weighted least squares of the difference between the measured counts $N'_m$ and modeled counts $N_m$, i.e., $$\varphi = \sum_i \frac{(\tilde{N}_i - \vec{N}_i)^2}{\sigma_i^2},$$

wherein $\sigma_i$ is the standard deviation of the measured count $\tilde{N}_i$.

Alternatively, the comparison can be any known distance measure, e.g., a Euclidean distance, or error measure between the measured and decomposed counts.

The decomposed counts $\vec{N}(\hat{L})$ can be obtained from a calculation, e.g., using the formula $$N_i = C \int_{E_i}^{E_{i+1}} dE S_0(E)\exp[-\mu_1(E)L_1 - \mu_2(E)L_2],$$

wherein C is a calibration constant. In certain implementations, the above formula can be modified to include the detector response. As discussed in U.S. patent application Ser. No. 13/866,965, incorporated herein by reference in its entirety, the response function of the radiation detectors can be calibrated to provide improved results. In one implementation, the detector model for the number of counts of each given radiation detector is $$N_i = Tne^{-n\tau}\!\!\int\!\!\int dE\, dE_0 R_0(E,E_0)S(E_0) + Tn^2e^{-n\tau}\!\!\int\!\!\int\!\!\int dE\, dE_0 dE_1 R_1(E,E_0,E_1)S(E_0)S(E_1),$$

wherein each of the integrating time T, the linear response function $R_0$, the nonlinear response function $R_1$, and the dead time r are known for each radiation detector and energy component as a result of calibrations performed before the projective measurements on an object OBJ.

Further, the decomposed counts $\vec{N}(\vec{L})$ can be obtained by performing various calibrations to measure and store the counts of various known lengths of material phantoms, and interpolating among these counts to determine counts for lengths in between the lengths of the material phantoms.

Additionally, the decomposed counts $\vec{N}(\vec{L})$ can be provided and stored in a lookup table (LUT). Further, the LUT can be indexed by the projection lengths $\vec{L}$. That is, $\vec{N}(\vec{L})=\text{LUT}(\vec{L})$.

The objective function φ can be used to formulate an optimization problem by adjusting the projection lengths $\vec{L}$ until the value of the objective function φ is minimized, i.e., $$\min_{\vec{L}} \varphi(\tilde{N}, N(\vec{L})).$$

The minimum value of the objective function φ can then be returned to represent an estimate quantifying the PVE. That is, when the PVE is small, then a value of $N(\vec{L})$ can be found that closely agrees with the measured counts $\tilde{N}$, and the value of the objective function φ will approach a minimum of zero, for example. However, when only poor agreement can be obtained between $N(\vec{L})$ and the measured counts $\tilde{N}$, this poor agreement might be due to PVE, and the value of the objective function φ will not approach zero. Accordingly, when the agreement is poor, one approach to obtain better agreement is to decrease the pixel sizes from a macro-pixel to micro-pixels and repeat the material decomposition again using the micro-pixels, instead.

In certain implementations, the predetermined predicted values $\vec{N}(\vec{L})$ in the LUT can be values of N calculated based on basis material path lengths of expected materials, either singularly or in combination with one or more additional materials (e.g., the materials can be bone and soft tissue, which is primarily composed of water). The values of $\vec{N}(\vec{L})$ can be generated via simulation programs or empirically (e.g., using calibration measurements of the known material phantoms). The macro-pixel 125 value can be used to estimate the path lengths of the constituent basis materials in the scan, for example a combination of the first material 105 and the second material 110.

In step S303, the results from the comparison of the macro-pixel counts $\tilde{N}$ to a calculated/calibrated counts $N(\vec{L})$ (e.g., the minimum value of an objective function φ) is compared to a predefined threshold. When the minimum value of the objective function φ is less than the predefined threshold, then it is determined that no PVE correction is to be performed, and the method continues from step S303 to step S305. Otherwise, it is determined that PVE correction is to be performed, and the method continues from step S303 to step S307.

In certain implementations, the LUT can contain a set L={ $\vec{L}_1, \vec{L}_2, \ldots, \vec{L}_k$} of basis material path lengths for their corresponding macro-pixel 130 measurements, $\vec{N}$, wherein $$\vec{N}=\text{LUT}(\vec{L}).$$

A search is perform on the LUT to find the argument $\vec{L}$ that minimizes the disagreement, i.e., $$\min_{\vec{L}} \|\tilde{N} - LUT(\vec{L})\|.$$

A predefined threshold, ∈, is applied to the minimized difference between subsequent macro-pixel measurements, $\tilde{N}$, and the values in the LUT, such that PVE corrections are performed when the inequality $$\|\tilde{N}-\text{LUT}(\vec{L})\| \le \in$$

is not satisfied.

To reach step S307, it has been determined a difference measure between $\tilde{N}$ and $\vec{N}$ for the macro-pixel 125 is outside the predetermined deviation range (e.g., greater than the predefined threshold ∈) from the value in the LUT. Accordingly, a partial volume error (PVE) has been identified, and the micro-pixel measurements are used instead of the macro-pixel measurement to provide better spatial resolution of the different material components. The micro-pixel 130 measurements can be decomposed into material components (e.g., projection lengths $\vec{L}$) using the same method as used for the macro-pixel 125. For example, the measured counts can be given by $\tilde{N}=4 \times \{N_1^{(micro)}, N_2^{(micro)}, \ldots, N_n^{(micro)}\}$, wherein the factor 4 accounts for the fact that a micro-pixel 130 is four times smaller than the macro-pixel 125. Therefore, to use the LUT, which is based on/calibrated for the macro-pixel 125, the counts are to be scaled up by the number of micro-pixels 130 per macro-pixel 125. Then, the material decomposition can be solved for each of the macro-pixels 125 by solving, e.g., the optimization problem $$\min_{\vec{L}} \|\tilde{N} - LUT(\vec{L})\|.$$

Other methods of performing the material decomposition on the micro-pixel measurement can be used without deviating for the spirit of the invention.

The threshold e can be a predetermined value greater than or less than the value in the LUT, for example, ±1%, ±10%, ±20%, ±30%, or ±50%.

It may be appreciated that interpolation of the LUT may be based on the arguments of the LUT, for example $L_1$ and $L_2$. Alternatively, the arguments of the LUT may be p and L, wherein $L=L_1+L_2$, $L_1=p*L$, and $L_2=(1-p)*L$. Interpolation may be performed between L values. For example, to determine the value for $L_1=2.5$ and $L_2=1.5$, the value in the LUT may not be provided because the lookup table is discretized at integer values of the projection lengths (i.e., $L_1=\{0,1,2,\ldots,N\}$ and $L_2=\{0,1,2,\ldots,N)\}$. Thus, a linear interpolation may be performed by determining an average LUT value between the discretized values neighboring said $L_1$ and $L_2$ values, e.g., $$LUT(L_1=2.5, L_2=1.5) = \frac{LUT(2,1) + LUT(3,1) + LUT(2,2) + LUT(3,2)}{4}.$$

In step S305, material images are reconstructed from the material decomposition of the projection images.

In certain implementations, the reconstruction can use different spatial grid sizes depending on the spatial distribution of which macro-pixels were selected for the material decomposition to be performed using micro-pixel measurements. That is, in regions where micro-pixel measurements were used for material decomposition, the material-decomposed projection data can be resolved as the micro-pixel resolution. In regions where macro-pixel measurements were used for material decomposition, the material-decomposed projection data can be resolved as the macro-pixel resolution.

In certain implementations, the reconstruction can be performed using a uniform spatial grid size corresponding to the macro-pixel resolution. For example, in regions where micro-pixel measurements were used for material decomposition, the projection lengths of the micro-pixels can be averaged to generate average projection lengths for the macro-pixel, and these average projection lengths for the macro-pixel can be used for the image reconstruction.

In certain implementations, a communications bottleneck can result in too little data bandwidth to send all of the micro-pixel data across a slip-ring to a fixed portion of a CT gantry. In this case, a comparison/difference between the measured counts of a given macro-pixel and the closest count values in a LUT can be used as a quick check on whether the macro-pixel counts represent a PVE. For those macro-pixels in which the difference between the measured counts and the closest counts in the LUT exceed a threshold, the macro-pixel can be flagged and the micro-pixel counts for that macro-pixel can be included in the data communicated across the slip ring to be process later during the material decomposition process. When only a small subset of the macro-pixels exceed the PVE threshold e, then the increase in the amount of data communicated across the slip ring will be negligible, especially compared to the increase if all of the micro-pixel counts were communicated across the slip ring.

In certain implementations, the values from the macro-pixels that are less than the threshold ∈, and the values from the micro-pixels corresponding to macro-pixel measurements that are greater than the threshold ∈, are then utilized to reconstruct the scanned image in step S305. That is, macro-pixels that are not affected by PVEs are processed during reconstruction at the coarser macro-pixel resolution, and macro-pixels that are affected by PVEs are processed at the finer micro-pixel resolution.

In certain implementations, the selection of a value for the predefined threshold ∈ can be determined empirically. For example, adjustment of the threshold value ∈ can change the percentage of macro-pixels 125 that are identified as potentially having PVEs that are to be corrected using the micro-pixel counts. As the predefined threshold ∈ is made smaller, there will be a point of diminishing returns below which only small gains in image-quality can be achieved. Further, the selection of a value for the predefined threshold ∈ can be guided by a maximum communications bandwidth between the rotating and stationary portions of the CT scanner. used for the calculations during image reconstruction and thus adjusts transmission bandwidth demand and processing time.

In certain implementations, the material decomposition can be performed up until a first convergence criterion is satisfied in order to determine at step S303 whether the predefined threshold ∈ exceeds the difference/disagreement between the projection-lengths based counts $\vec{N}$ and the measured counts $\tilde{N}$. Then the projection-lengths $\vec{L}$ from this initial decomposition can be stored and later used in step S305 or step S307 for a second material decomposition can be performed up until a second convergence criterion. For example, in the second material decomposition results from a LUT can be interpolated to more precisely determine the projection-lengths $\vec{L}$. Additionally, any known method of material decomposition can be used for the first and second material decompositions.

In certain implementations, the material decomposition is performed only once for each macro-pixel, in step S301, and when material decomposition is performed on a micro-pixel, it is only performed once for the macro-pixel, in step S307.

In step S305, the material-component images can be reconstructed from the material-component projection data generated by decomposing the spectral projection data for the macro-pixels and for select micro-pixels into material components. Any known method of image reconstruction can be used. For example, the image reconstruction process can be performed using any of a filtered back-projection method, iterative image reconstruction methods (e.g., using a total variation minimization regularization term), a Fourier-based reconstruction method, or stochastic image reconstruction methods.

The above description illustrates the methods described herein using the non-limiting example of PCDs. However, without deviating from the spirit of the methods described herein, these methods can also be implemented using other types of X-ray detectors including e.g., energy integrating detectors in which signals from respective smaller detectors (e.g., micro-pixels) are aggregated to generate a signal for a virtual larger detector (e.g., a macro-pixel).

Figure 5:
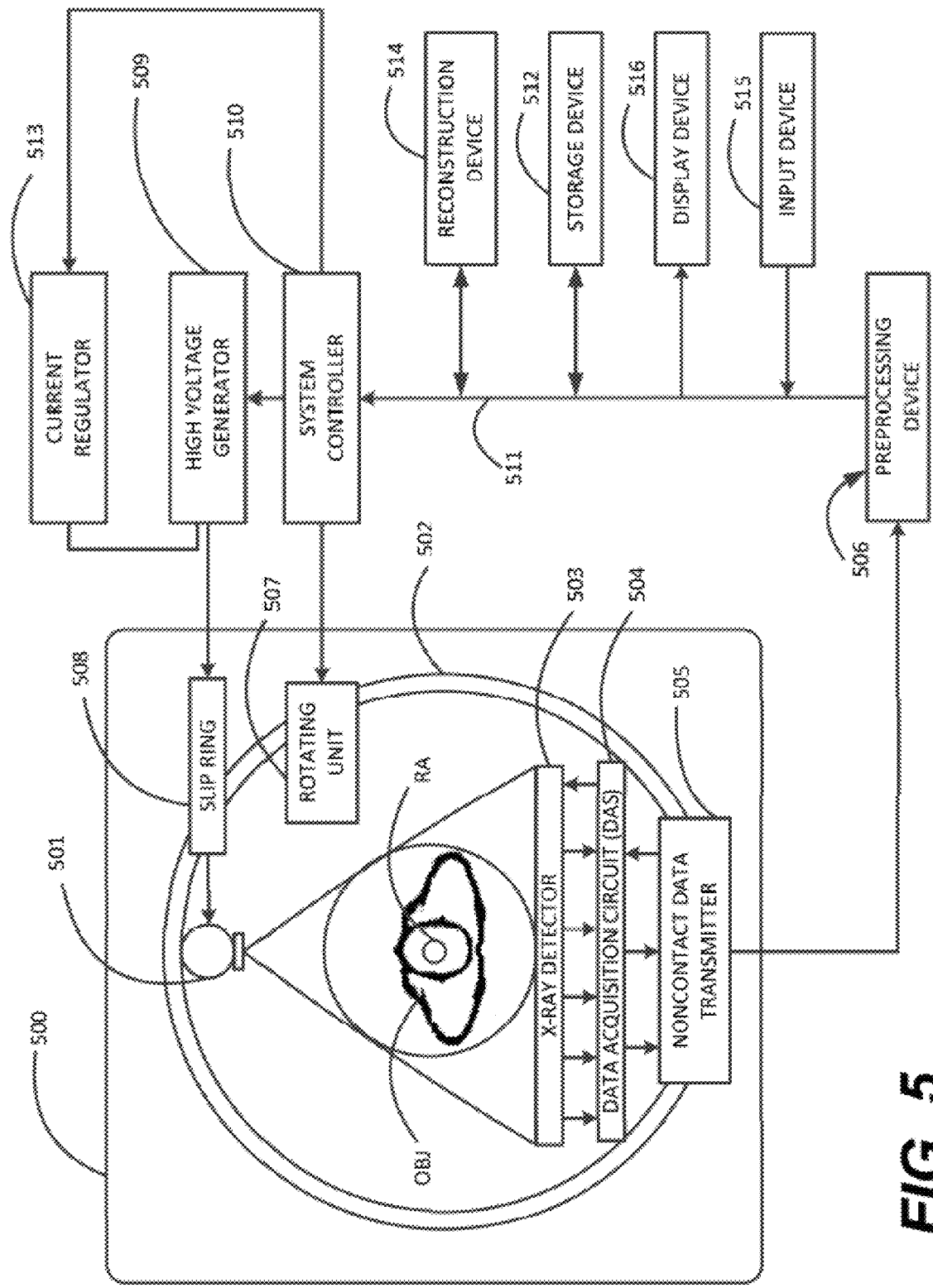
FIG. 5 illustrates a schematic of an implementation of a computed tomography scanner, according to an exemplary embodiment of the disclosure.

FIG. 5 shows a schematic of an implementation of a CT scanner according to an exemplary embodiment of the disclosure. Referring to FIG. 5, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA (or an axis of rotation). A rotating unit 507 rotates the annular frame 502 at a high speed, such as 0.4 sec/rotation, while the object OBJ is being moved along the axis RA into or out of the illustrated page.

X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. The rotate/rotate type will be used as an example for purposes of clarity.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS)

504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing, for example, various steps of the methods 110, 150, 200, and 300 for training a neural network and reducing imaging artifacts.

The reconstruction device 514 can execute various steps of the methods 110, 150, 200, and 300. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can implement various of the steps of methods 110, 150, 200, and 300 in addition to various CT image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

While certain implementations have been described, these implementations have been presented by way of example only, and are not intended to limit the teachings of this disclosure. Indeed, the novel methods, apparatuses and systems described herein can be embodied in a variety of other forms; furthermore, various omissions, substitutions and changes in the form of the methods, apparatuses and systems described herein can be made without departing from the spirit of this disclosure.

The invention claimed is:

1. An imaging apparatus, comprising:
circuitry configured to
  obtain projection data representing an intensity of radiation detected at a plurality of detector elements,
  combine, for each macro-pixel corresponding to a respective grouping of detector elements of the plurality of detector elements, the projection data corresponding to each macro-pixel to generate another projection data,
  perform material decomposition, for each macro-pixel, on the another projection data to generate first material-decomposed projection data, select, for partial-volume-error (PVE) correction, macro-pixels for which the material decomposition fails to converge below a predefined threshold, perform the PVE correction on the selected macro-pixels to generate corrected material-decomposed projection data, and reconstruct material-component images from the corrected material-decomposed projection data.

2. The imaging apparatus according to claim 1, wherein the circuitry is further configured to perform the material decomposition by, for each macro-pixel of the macro-pixels, minimizing a disagreement between the another projection data and an estimate of the another projection data corresponding to the each macro-pixel, wherein the estimate of the another projection data is based on projection lengths of respective material components, and select the macro-pixels for the PVE correction based on whether the disagreement between the another projection data and the estimate exceeds a predefined threshold.

3. The imaging apparatus according to claim 1, wherein the circuitry is further configured to perform the PVE correction by performing material decomposition on values of the projection data corresponding to the macro-pixels selected for the PVE correction to generate second material-decomposed projection data, which has a spatial resolution of the plurality of detector elements, whereas the first material-decomposed projection data has a resolution of the macro-pixels, wherein the corrected material-decomposed projection data includes the second material-decomposed projection data for the macro-pixels selected for the PVE correction and includes the first material-decomposed projection data for macro-pixels not selected for the PVE correction.

4. The imaging apparatus according to claim 3, wherein the circuitry is further configured to reconstruct the material-component images using the second material-decomposed projection data for the macro-pixels selected for the PVE correction and using the first material-decomposed projection data for the macro-pixels not selected for the PVE correction.

5. The imaging apparatus according to claim 1, wherein the circuitry is further configured to perform the PVE correction by performing material decomposition on values of the projection data corresponding to the macro-pixels selected for the PVE correction to generate second material-decomposed projection data, which has a spatial resolution of the plurality of detector elements, whereas the first material-decomposed projection data has a resolution of the macro-pixels, and combine, for each macro-pixel of the macro-pixels, values of the second material-decomposed projection data corresponding to detector elements of the each of the macro-pixel to replace values of the first material-decomposed projection data corresponding to the each of the macro-pixel, thereby generating the corrected material-decomposed projection data.

6. The imaging apparatus according to claim 1, wherein the circuitry is further configured to obtain the projection data, wherein the projection data represents counts of gamma rays that are resolved according to respective energy bins, and combine the projection data corresponding to the each macro-pixel by summing, for each of the respective energy bins, counts of the projection data corresponding to the each macro-pixel to generate first counts.

7. The imaging apparatus according to claim 6, wherein the circuitry is further configured to perform the material decomposition by determining a count of detected X-rays for each of the respective energy bins based on projection lengths of two or more material components, determining a value of an objective function that represents a measure of a difference between the determined counts based on the projection lengths and the counts of the projection data corresponding to the each macro-pixel, and iteratively adjusting the projection lengths to minimize the value of the objective function until a convergence criterion is satisfied.

8. The imaging apparatus according to claim 7, wherein the circuitry is further configured to select the macro-pixels for the PVE correction by determining that the each macro-pixel is included in the macro-pixels for the PVE correction, when the minimized value of the objective function exceeds a pre-defined threshold, and determining that the each macro-pixel is not included in the macro-pixels for the PVE correction, when the minimized value of the objective function does not exceed the pre-defined threshold.

9. The imaging apparatus according to claim 6, wherein the circuitry is further configured to perform the material decomposition by selecting second counts from a lookup table to minimize a measure of a difference between the first counts and the second counts, the lookup table including counts that are grouped according to respective values of projection lengths of material components.

10. The imaging apparatus according to claim 1, further comprising a rotating member including a memory that stores the projection data; and a stator, wherein the rotating member transmits values of the projection data for each of the selected macro-pixels.

11. The imaging apparatus according to claim 10, wherein the rotating member transmits to the stator values of the another projection data for each of the macro-pixels for which the material decomposition converges below the predefined threshold.

12. The imaging apparatus according to claim 10, wherein the rotating member transmits to the stator values of the another projection data for all of the macro-pixels, and a part of the circuitry that is on the stator is configured to select the selected macro-pixels for which the material decomposition fails to converge below the pre-defined threshold, send, to the rotating member, a transmission request requesting a transmission of the values of the projection data corresponding to the selected macro-pixels, receive, from the rotating member, the a transmission of the values of the projection data corresponding to the selected macro-pixels, perform the PVE correction on the selected macro-pixels to generate corrected material-decomposed projection data, and reconstruct material-component images from the corrected material-decomposed projection data.

13. An X-ray imaging apparatus, comprising:
an X-ray source configured to radiate X-rays through an object space configured to accommodate an object or subject to be imaged;
a plurality of detector elements arranged across the object space and opposite to the X-ray source, the plurality of detector elements being configured to detect the X-rays from the X-ray source, and the plurality of detector elements configured to generate projection data representing counts of the X-rays resolved according to energy bins; and
first circuitry configured to
  combine, for each macro-pixel corresponding to a respective grouping of detector elements of the plurality of detector elements, the projection data corresponding to each macro-pixel to generate another projection data,
  perform material decomposition, for each macro-pixel, on the another projection data to generate material-decomposed projection data,
  select, for partial-volume-error (PVE) correction, macro-pixels for which the material decomposition fails to converge below a predefined threshold, and
  perform the PVE correction on the selected macro-pixels to generate corrected material-decomposed projection data; and
second circuitry configured to
  obtain the corrected material-decomposed projection data, and
  reconstruct material-component images from the corrected material-decomposed projection data.

14. An imaging method, comprising:
obtaining projection data representing an intensity of radiation detected at a plurality of detector elements,
combining, for each macro-pixel corresponding to a respective grouping of detector elements of the plurality of detector elements, the projection data corresponding to each macro-pixel to generate another projection data,
performing material decomposition, for each macro-pixel, on the another projection data to generate material-decomposed projection data,
selecting, for partial-volume-error (PVE) correction, macro-pixels for which the material decomposition fails to converge below a predefined threshold,
performing the PVE correction on the selected macro-pixels to generate corrected material-decomposed projection data, and
reconstructing material-component images from the corrected material-decomposed projection data.

15. The method according to claim 14, wherein
the performing of the material decomposition further includes minimizing, for each macro-pixel of the macro-pixels, a disagreement between the another projection data and an estimate of the another projection data corresponding to the each macro-pixel, wherein the estimate of the another projection data is based on projection lengths of respective material components, and
the selecting of the macro-pixels for the PVE correction is based on whether the disagreement between the another projection data and the estimate exceeds a predefined threshold.

16. The method according to claim 14, wherein the performing of the PVE correction further includes performing material decomposition on values of the projection data corresponding to the macro-pixels selected for the PVE correction to generate second material-decomposed projection data, which has a spatial resolution of the plurality of detector elements, whereas the first material-decomposed projection data has a resolution of the macro-pixels, wherein the corrected material-decomposed projection data includes the second material-decomposed projection data for the macro-pixels selected for the PVE correction and includes the first material-decomposed projection data for macro-pixels not selected for the PVE correction.

17. The method according to claim 16, wherein the reconstructing of the material-component images is performed using the fine-resolution material-decomposed projection data for the macro-pixels selected for the PVE correction and using the material-decomposed projection data for the macro-pixels not selected for the PVE correction.

18. The method according to claim 14, wherein
the performing of the PVE correction includes performing material decomposition on values of the projection data corresponding to the macro-pixels selected for the PVE correction to generate second material-decomposed projection data, which has a spatial resolution of the plurality of detector elements, whereas the first material-decomposed projection data has a resolution of the macro-pixels, and combine, for each macro-pixel of the macro-pixels, values of the second material-decomposed projection data corresponding to detector elements of the each of the macro-pixel to replace values of the first material-decomposed projection data corresponding to the each of the macro-pixel, thereby generating the corrected material-decomposed projection data.

19. The method according to claim 14, wherein
the obtaining of the projection data further includes that the projection data represents counts of gamma rays that are resolved according to respective energy bins, and
the combining of the projection data for the each macro-pixel is performed by summing, for each of the respective energy bins, counts of the projection data corresponding to the each macro-pixel to generate first counts.

20. The method according to claim 19, wherein the performing of the material decomposition includes
determining a count of detected X-rays for each of the respective energy bins based on projection lengths of two or more material components,
determining a value of an objective function that represents a measure of a difference between the determined counts based on the projection lengths and the counts of the projection data corresponding to the each macro-pixel, and
iteratively adjusting the projection lengths to minimize the value of the objective function until a convergence criterion is satisfied.

21. The method according to claim 20, wherein the selecting of the macro-pixels for the PVE correction includes
determining that the each macro-pixel is included in the macro-pixels for the PVE correction, when the minimized value of the objective function exceeds a predefined threshold, and
determining that the each macro-pixel is not included in the macro-pixels for the PVE correction, when the minimized value of the objective function does not exceed the pre-defined threshold.

22. The method according to claim 19, wherein the performing of the material decomposition includes selecting second counts from a lookup table to minimize a measure of a difference between the first counts and the second counts, the lookup table including counts that are grouped according to respective values of projection lengths of material components.

23. A non-transitory computer-readable medium storing executable instructions, wherein the instructions, when executed by processing circuitry, cause the processing circuitry to perform the method according to claim 14.

* * * * *